(12) United States Patent
Okamoto et al.

(10) Patent No.: US 7,598,411 B2
(45) Date of Patent: Oct. 6, 2009

(54) PROCESSES FOR PRODUCING CARBONIC ESTER AND PRODUCING POLYCARBONATE

(75) Inventors: Masaya Okamoto, Ibaraki (JP); Jun-ichi Sugiyama, Ibaraki (JP); Mitsuru Ueda, Ibaraki (JP)

(73) Assignees: National Institute of Advanced Industrial Science and Technology, Tokyo (JP); Idemitsu Kosan Co., Ltd., Tokyo (JP)

( * ) Notice: Subject to any disclaimer, the term of this patent is extended or adjusted under 35 U.S.C. 154(b) by 803 days.

(21) Appl. No.: 10/509,340

(22) PCT Filed: Mar. 27, 2003

(86) PCT No.: PCT/JP03/03831

§ 371 (c)(1), (2), (4) Date: Oct. 8, 2004

(87) PCT Pub. No.: WO03/087030

PCT Pub. Date: Oct. 23, 2003

(65) Prior Publication Data

US 2005/0234259 A1    Oct. 20, 2005

(30) Foreign Application Priority Data

Apr. 15, 2002 (JP) .................... 2002-112180
Jun. 27, 2002 (JP) .................... 2002-188215

(51) Int. Cl.
*C07C 69/9699* (2006.01)
(52) U.S. Cl. ............................ 558/274; 558/277
(58) Field of Classification Search .......... 558/274, 558/277
See application file for complete search history.

(56) References Cited

U.S. PATENT DOCUMENTS

| 4,096,169 | A | * | 6/1978 | Chalk ..................... 558/268 |
| 5,284,964 | A | * | 2/1994 | Pressman et al. ........ 558/260 |
| 5,502,232 | A | | 3/1996 | Buysch et al. |
| 5,760,272 | A | | 6/1998 | Pressman et al. |

FOREIGN PATENT DOCUMENTS

| EP | 0 350 700 A2 | | 1/1990 |
| EP | 0 869 110 A1 | * | 7/1998 |
| EP | 869110 | | 10/1998 |
| JP | 05-310637 | | 11/1993 |
| JP | 10-139708 | | 5/1998 |
| JP | 11-292962 | | 10/1999 |
| JP | 2000-297148 | | 10/2000 |
| JP | 2002-069170 | | 3/2002 |

* cited by examiner

*Primary Examiner*—James O Wilson
*Assistant Examiner*—Ebenezer Sackey
(74) *Attorney, Agent, or Firm*—Oblon, Spivak, McClelland, Maier & Neustadt, L.L.P.

(57) ABSTRACT

A process for producing a carbonic ester, characterized in that an aromatic monohydroxy compound or an aliphatic monohydroxy compound is subjected to oxidative carbonylation with carbon monoxide and oxygen in the presence of a palladium catalyst using a compound having a carbonate bond as a reaction solvent. A process for producing a polycarbonate, characterized in that an aromatic dihydroxy compound or an aliphatic dihydroxy compound is subjected to oxidative carbonylation with carbon monoxide and oxygen in the presence of a palladium catalyst using a compound having a carbonate bond as a reaction solvent is also described. The carbonic ester can be produced with a higher yield and at a higher reaction rate and, also, a polycarbonate having a higher molecular weight as compared with the conventional method can be produced with a higher yield and at a higher reaction rate.

10 Claims, No Drawings

US 7,598,411 B2

PROCESSES FOR PRODUCING CARBONIC ESTER AND PRODUCING POLYCARBONATE

TECHNICAL FIELD

The present invention relates to a process for producing a carbonic ester from an aromatic monohydroxy compound or an aliphatic monohydroxy compound and to a process for producing a polycarbonate from an aromatic dihydroxy compound or an aliphatic dihydroxy compound. More specifically, the present invention is directed to a process for producing an aromatic carbonic ester or an aliphatic carbonic ester with a high efficiency by an oxidative carbonylation reaction of an aromatic monohydroxy compound or an aliphatic monohydroxy compound with carbon monoxide and oxygen using a palladium catalyst and a specific reaction solvent, and to a process for producing a polycarbonate with a high efficiency by an oxidative carbonylation reaction of an aromatic dihydroxy compound or an aliphatic dihydroxy compound with carbon monoxide and oxygen using a palladium catalyst and a specific reaction solvent.

Aromatic carbonic esters are useful as intermediates for the synthesis of various organic compounds such as the synthesis of polycarbonates by an ester interchange method, and also as raw materials for polycarbonate resins, etc. Aliphatic carbonic esters are useful as solvents for resins, paints, etc., as alkylation agents, as carbonylation agents, and as raw materials for polycarbonate resins, etc.

Polycarbonates are useful as resin materials used in the electric or electronic field, automobile field, optical part field, structural material field, etc.

BACKGROUND ART

As a process for producing an aromatic carbonic ester, there is generally known a process in which an aromatic monohydroxy compound such as phenol is reacted with phosgene in the presence of an alkali. This process, however, has a problem that deadly poisonous phosgene must be used and that a stoichiometric amount of an alkali salt is produced as a by-product.

Also known is a process for producing an aromatic carbonic ester by an ester interchange reaction of an aliphatic carbonic ester with an aromatic monohydroxy compound. Because this method requires continuous removal, by distillation, of an aliphatic alcohol or an aromatic alcohol produced as a by-product in order to proceed with the ester interchange reaction, a large amount of thermal energy is lost. Further, this process requires complicated steps and, thus, has a problem that the manufacturing steps as a whole, including a raw material preparation step and a by-product recycling step, are not economical.

Under these circumstances, development of a simple method for the production of a carbonic ester is desired. Thus, a process for producing an aromatic carbonic ester is proposed in which an aromatic monohydroxy compound to be esterified is subjected to oxidative carbonylation with carbon monoxide and oxygen in the presence of a catalyst. As typical catalysts used in this method, there are proposed a catalyst in which a palladium compound is combined with a copper compound and a base (Japanese Examined Patent Publications Nos. S61-8816 and S61-43338), a system in which a quinoline and an ammonium salt organ alkali metal or alkaline earth metal halide are used in addition to a palladium compound and a promoter (Japanese Unexamined Patent Publications Nos. S54-135743, S54-135744, H02-104564, H02-142754, H06-9505, H06-172268, H06-172269, H06-271506, H06-271509, Japanese Examined Patent Publication No. H06-57678, Japanese Unexamined Patent Publications Nos. H08-89810 and H08-193056), a catalyst system including a palladium compound, an alkali metal or alkaline earth metal halide, an iodide or an onium iodide compound and zeolite (Japanese Unexamined Patent Publication No. H01-165551) and a catalyst system including a palladium compound, an alkali metal or alkaline earth metal halide and activated carbon (Japanese Unexamined Patent Publication No. H08-92168). These catalysts are not fully satisfactory from the standpoint of economy with respect to the reaction rate of the oxidative carbonylation reaction. There is also proposed a method in which a palladium compound, a copper or lanthanoide compound, 2-hydroxypyridine and an aprotonic polar solvent are used (Japanese Unexamined Patent Publication No. H09-110804). Mainly because of the disuse of a solvent for the reaction, the yield of the method is low. Whilst the reaction proceeds using a halogenated organic solvent such as dichloromethane, the halogenated organic solvent is considered to adversely affect the environment.

As a process for producing a polycarbonate, there are generally known a method (solution method) in which an aromatic dihydroxy compound such as bisphenol A is directly reacted with phosgene, a method (ester interchange method) in which an aromatic dihydroxy compound such as bisphenol A is subjected to ester interchange with a carbonic diester such as diphenyl carbonate, and a method (melt method) in which a carbonic diester such as diphenyl carbonate is used as a carbonyl source and is heated and melted for reaction. However, the solution method has a problem that poisonous phosgene must be used and that the production apparatus is corroded by by-product chlorine-containing compounds such as hydrogen chloride and sodium chloride. The ester interchange method requires complicated steps for the preparation of the carbonic diester raw material and that the manufacturing steps as a whole, including a raw material preparation step and a by-product recycling step, are not economical. The melt method requires heating for the production and melting of a carbonic diester and, thus, has a problem that the polycarbonate obtained is colored due to heating at elevated temperatures. As a process for producing an aromatic polycarbonate, there is disclosed, for example, a method in which an aromatic dihydroxy compound and carbon monoxide are reacted in the presence of a base and a selenium compound (Japanese Unexamined Patent Publication No. S55-92731). This method has a problem that selenium is deadly poisonous and that the reaction, which is a stoichiometric reaction, requires a large amount of selenium. As a new process for producing a polycarbonate, there is proposed a method by an oxidative carbonylation reaction using a palladium/redox agent/halogenated onium salt catalyst (for example, Japanese Unexamined Patent Publication No. S53-68744). With this method, only an oligocarbonate having a low degree of polymerization is obtained because the reaction rate is not sufficiently rapid. Another problem of this method is that a halogenated organic solvent which is considered to adversely affect the environment is used as a reaction solvent. With the foregoing background, production of a polycarbonate in an efficient and safe manner without adversely affecting the environment is desired.

DISCLOSURE OF THE INVENTION

It is an object of the present invention to provide a process which can solve the problems of the conventional methods for producing a carbonic ester and which can efficiently produce a carbonic diester from an aromatic monohydroxy compound or an aliphatic monohydroxy compound with a high yield without using phosgene or chlorine gas and without using a halogen-containing organic solvent as a reaction solvent.

It is also an object of the present invention to provide a process which can solve the problems of the conventional methods for producing a polycarbonate having a high molecular weight and which can efficiently produce a polycarbonate from an aromatic dihydroxy compound or an aliphatic dihydroxy compound in one step with a high yield without using phosgene or chlorine gas and without using a halogen-containing organic solvent as a reaction solvent.

The present inventors have made an earnest study and have found that the above objects can be extremely suitably accomplished by reacting an aromatic monohydroxy compound or an aliphatic monohydroxy compound with carbon monoxide and oxygen in the presence of a palladium catalyst using a specific reaction solvent and, particularly, by using zeolite having a particle diameter of 300 μm or smaller as a dehydrating agent. The present invention has been achieved by the above finding.

Also, the present inventors have made an earnest study and have found that the above objects can be accomplished by reacting an aromatic dihydroxy compound or an aliphatic dihydroxy compound with carbon monoxide and oxygen in the presence of a palladium catalyst using a specific reaction solvent. The present invention has been achieved by the above finding.

Namely, the present invention provides a process for producing a carbonic ester as follows.

1. A process for producing a carbonic ester, characterized in that an aromatic monohydroxy compound or an aliphatic monohydroxy compound is subjected to oxidative carbonylation with carbon monoxide and oxygen in the presence of a palladium catalyst using a compound having a carbonate bond as a reaction solvent.
2. A process for producing a carbonic ester as defined in item 1 above, wherein the aromatic monohydroxy compound or aliphatic monohydroxy compound is subjected to oxidative carbonylation with carbon monoxide and oxygen in the presence of the palladium catalyst and a promoter using the compound having a carbonate bond as the reaction solvent.
3. A process for producing a carbonic ester as defined in item 2 above, wherein the promoter is a redox catalyst.
4. A process for producing a carbonic ester as defined in item 2 or 3 above, wherein the promoter is an organic salt for activating the aromatic monohydroxy compound or aliphatic monohydroxy compound.
5. A process for producing a carbonic ester as defined in items 1 through 4 above, wherein the oxidative carbonylation is carried out in a further presence of a dehydrating agent.
6. A process for producing a carbonic ester as defined in items 1 through 5 above, wherein the reaction solvent compound having a carbonate bond is a compound selected from the group consisting of dimethyl carbonate, diethyl carbonate, diphenyl carbonate, ethylene carbonate, propylene carbonate, diallyl carbonate, allyl methyl carbonate, bis(2-methoxyphenyl) carbonate, vinylene carbonate, dibenzyl carbonate, di-(o-methoxyphenyl) carbonate and methyl ethyl carbonate.
7. A process for producing a carbonic ester as defined in items 1 through 6 above, wherein the compound having a carbonate bond is propylene carbonate.
8. A process for producing a carbonic ester, characterized in that an aromatic monohydroxy compound or an aliphatic monohydroxy compound is reacted with carbon monoxide and oxygen in the presence of (a) a palladium compound, (b) a compound having redox catalytic activity, (c) at least one onium salt selected from onium bromides and onium chlorides and (d) zeolite having a particle diameter of 300 μm or smaller.

Also, the present invention provides a process for producing a polycarbonate as follows.

9. A process for producing a polycarbonate, characterized in that an aromatic dihydroxy compound or an aliphatic dihydroxy compound is subjected to oxidative carbonylation with carbon monoxide and oxygen in the presence of a palladium catalyst using a compound having a carbonate bond as a reaction solvent.
10. A process for producing a polycarbonate as defined in item 9 above, wherein the aromatic dihydroxy compound or aliphatic dihydroxy compound is subjected to oxidative carbonylation with carbon monoxide and oxygen in the presence of the palladium catalyst and a promoter using the compound having a carbonate bond as the reaction solvent.
11. A process for producing a polycarbonate as defined in item 10 above, wherein the promoter is a redox catalyst.
12. A process for producing a polycarbonate as defined in item 10 or 11 above, wherein the promoter is an organic salt for activating the aromatic dihydroxy compound or aliphatic dihydroxy compound.
13. A process for producing a polycarbonate as defined in items 9 through 12 above, wherein the oxidative carbonylation is carried out in a further presence of a dehydrating agent.
14. A process for producing a polycarbonate as defined in items 9 through 13 above, wherein the reaction solvent compound having a carbonate bond is a compound selected from the group consisting of dimethyl carbonate, diethyl carbonate, diphenyl carbonate, ethylene carbonate, propylene carbonate, diallyl carbonate, allyl methyl carbonate, bis(2-methoxyphenyl) carbonate, vinylene carbonate, dibenzyl carbonate, di-(o-methoxyphenyl) carbonate and methyl ethyl carbonate.
15. A process for producing a polycarbonate as defined in items 9 through 14 above, wherein the compound having a carbonate bond is propylene carbonate.
16. A process for producing a polycarbonate, characterized in that an aromatic dihydroxy compound or an aliphatic dihydroxy compound is reacted with carbon monoxide and oxygen in the presence of (a) a palladium compound, (b) a compound having redox catalytic activity, (c) at least one onium salt selected from onium bromides and onium chlorides and (d) zeolite having a particle diameter of 300 μm or smaller.

PREFERRED EMBODIMENT FOR CARRYING OUT THE INVENTION

As the aromatic monohydroxy compound and aliphatic monohydroxy compound used as a raw material in the process for producing a carbonic ester according to the present invention, there may be used various conventionally known compounds shown below and may be suitably selected according to the desired carbonic ester.

The aromatic monohydroxy compound and aliphatic monohydroxy compound may be used singly or in combination of two or more and, further, may be used together with a dihydroxy compound such as bisphenol A or ethylene glycol.

First, the aromatic monohydroxy compound may be an aromatic monohydroxy compound (monohydric phenol)

having 6-26 carbon atoms and represented by the following general formula (I):

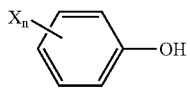

wherein n is an integer of from 0 to 5 and X represents a halogen atom (such as chlorine, bromine, fluorine or iodine), an alkyl or alkoxy group having from 1 to 10 carbon atoms, an aryl group having from 6 to 20 carbon atoms, an aralkyl group having from 7 to 20 carbon atoms, a cyano group or an ester group and may be positioned at any of o-, m- and p-positions. Specific examples of the aromatic monohydroxy compound include phenols such as phenol, o-, m- and p-cresol, p-tert-butylphenol, p-tert-octylphenol, p-tert-amylphenol, p-α-cumylphenol, methoxyphenol, chlorophenol, trichlorophenol, bromophenol, tribromophenol, fluorophenol and cyanophenol.

The aliphatic monohydroxy compound may be an aliphatic monohydroxy compound represented by the following general formula (II):

R'OH        (II)

wherein R' represents an aliphatic alkyl group having from 1 to 20 carbon atoms. The group R' may be primary, secondary or tertiary and may contain a branched structure, a cyclic structure or a halogen atom as appropriate.

Specific examples of the aliphatic monohydroxy compound include methanol, ethanol, 1-propanol, 2-propanol, 2-chloro-1-propanol, 1-chloro-2-propanol, 1-butanol, 2-butanol, isobutanol, tert-butanol, 1-pentanol, 2-methyl-1-butanol, 3-methyl-1-butanol, 2,2-dimethyl-1-propanol, cyclopentanol, 1-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, 3-ethyl-1-butanol, cyclohexanol, 1-octanol, 2-octanol, 2-ethyl-1-hexanol, 1-decanol, 2-decanol, 1-dodecanol, 2-dodecanol, 1-tetradecanol, 2-tetradecanol, 1-hexadecanol, 2-hexadecanol, 1-octadecanol, 2-octadecanol and benzyl alcohol.

In the process for producing carbonic ester according to the present invention, it is important that an aromatic monohydroxy compound or an aliphatic monohydroxy compound should be reacted with carbon monoxide and oxygen using a compound having a carbonate bond as a reaction solvent. Although any compound having a carbonate bond may be used as the reaction solvent, the compound must be liquid at the reaction temperature. As the reaction solvent, there may be mentioned, for example, dimethyl carbonate, diethyl carbonate, diphenyl carbonate, ethylene carbonate, propylene carbonate, diallyl carbonate, allyl methyl carbonate, bis(2-methoxyphenyl) carbonate, vinylene carbonate, dibenzyl carbonate, di-(o-methoxyphenyl) carbonate and methyl ethyl carbonate. Above all, propylene carbonate is preferable. These carbonate solvents may be used singly or in combination of two or more thereof.

In the present invention, the oxidative carbonylation reaction is carried out using the above-described compound having a carbonate bond as the reaction solvent. Therefore, the polymerization reaction can proceed very smoothly so that a carbonic ester can be obtained efficiently with a high yield as compared with the case in which an ordinary hydrocarbon solvent or an ether solvent is used. Unlike the conventionally employed halogen-containing organic solvent, there is no fear that the environment is adversely affected by the reaction solvent, since no halogen atom is contained therein.

The palladium catalyst used in the present invention is not specifically limited and a variety of palladium compounds may be used. Thus, ordinary palladium(II) chloride, palladium(II) bromide, palladium carbonyl chloride or palladium (II) acetate may be used.

As other palladium compounds usable as the palladium catalyst in the present invention, there may be further mentioned the following compounds.

(a) Polynuclear Metal Complex Compounds Having a Palladium Atom as a Metal Center and at Least One Atom Exhibiting Lewis Acidity Any polynuclear metal complex compound may be used as long as it has at least one atom capable of exhibiting Lewis acidity and a palladium atom. Specific examples of the compound include bis(diphenylphosphinomethane)(trichlorotin)dipalladium chloride,
bis(diphenylphosphinomethane)bis(trichlorotin)dipalladium,
bis(diphenylphosphinomethane)(trichlorotitanium)dipalladium chloride,
bis(diphenylphosphinomethane)bis(trichlorotitanium) dipalladium,
bis(diphenylphosphinomethane)(dichloroiron)dipalladium chloride,
bis(diphenylphosphinomethane)bis(dichloroiron)dipalladium,
bis(diphenylphosphinomethane)(trichlorotin)-(trichlorotitanium)dipalladium,
bis(diphenylphosphinomethane)(trichlorotin)-(dichloroiron) dipalladium,
bis(diphenylphosphinomethane)(trichlorotitanium)-(dichloroiron)dipalladium,
π-allyl(triphenylphosphine)(trichlorotin)palladium,
π-allyl(triphenylphosphine)(trichlorotitanium)palladium,
π-allyl(triphenylphosphine)(dichloroiron)palladium,
bis(trichlorotin)palladium,
bis(trichlorotitanium)palladium and
bis(dichloroiron)palladium.

A physical mixture of at least one atom exhibiting Lewis acidity and a compound having a palladium atom, which are precursors of the above polynuclear metal complex compounds, may be also used. Further, the above polynuclear metal complex compounds may be properly combined with a ligand such as an alkylphosphine, an aromatic phosphine, a phosphite or a phosphate and also with a nitrile ligand such as acetonitrile.

The polynuclear metal complex compound may be used by itself or in combination of two or more.

(b) Palladium Complex Compounds Containing as a Ligand an Organic Compound Having at Least Two Nitrogen Atoms As such palladium complex compounds, there may be mentioned palladium complex compounds having a bipyridyl compound as a ligand, palladium complex compounds having a diimine compound as a ligand, and palladium complex compounds having a diamine compound as a ligand.

Palladium complex compounds having a bipyridyl compound as a ligand may be complex compounds represented by the following general formula (III):

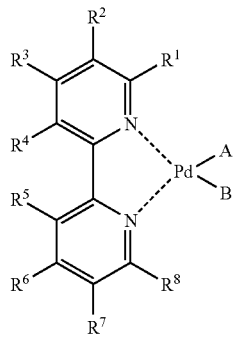

(III)

wherein $R^1$ to $R^8$ each independently represent an aliphatic hydrocarbon group having 1-20 carbon atoms, an aromatic group having from 6 to 20 carbon atoms in total and having a hydrocarbon group on the nucleus thereof, or a hydrogen atom; neighboring two substituents, such as $R^1$ and $R^2$, $R^2$ and $R^3$, $R^3$ and $R^4$, $R^4$ and $R^5$, $R^5$ and $R^6$, $R^6$ and $R^7$ and $R^7$ and $R^8$, are taken in combination to represent an aromatic ring, an aromatic ring containing a heteroatom such as a nitrogen atom, an oxygen atom or a phosphorus atom or an unsaturated aliphatic ring; A and B each independently represent a cyanate ion, an isocyanate ion, an azide ion, a nitrite ion, a chloride ion, a bromide ion, an iodide ion or an acetate ion; and A and B may be the same as or different from each other.

As the aliphatic hydrocarbon group having from 1 to 20 carbon atoms for $R^1$ to $R^8$ of the general formula (III), there may be mentioned a linear or branched alkyl group having from 1 to 20 carbon atoms and a cycloalkyl group having from 3 to 20 carbon atoms, specifically a methyl group, an ethyl group, an n-propyl group, an isopropyl group, an n-butyl group, an isobutyl group, a sec-butyl group, a tert-butyl group, a pentyl group, a hexyl group, an octyl group, a decyl group, a dodecyl group, a tetradecyl group, a hexadecyl group, an octadecyl group, a cyclopentyl group, a cyclohexyl group and a cyclooctyl group. A suitable substituent such as a lower alkyl group may be incorporated into the ring of the cycloalkyl group. As the aromatic group having from 6 to 20 carbon atoms in total and having a hydrocarbon group on the nucleus thereof, there may be mentioned, for example, an aromatic group, such as a phenyl group and a naphthyl group, and an aromatic group having an aromatic nucleus, such as phenyl or naphthyl, into which at least one linear, branched or cyclic alkyl group with 1 to 10 carbon atoms is introduced.

Palladium complex compounds having a diimine compound as a ligand may be a complex compound represented by the following general formula (IV):

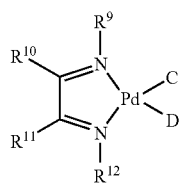

(IV)

wherein C and D each independently represent a cyanate ion, an isocyanate ion, an azide ion, a nitrite ion, a chloride ion, a bromide ion, an iodide ion or an acetate ion and may be the same as or different from each other, $R^9$ and $R^{12}$ each independently represent an aliphatic hydrocarbon group having from 1 to 20 carbon atoms or an aromatic group having from 7 to 20 carbon atoms in total and having a hydrocarbon group on the nucleus thereof, $R^9$ and $R^{12}$ may be the same as or different from each other, $R^{10}$ and $R^{11}$ each independently represent a hydrogen atom or a hydrocarbon group having from 1 to 20 carbon atoms, and $R^{10}$ and $R^{11}$ may be the same as or different from each other, or $R^{10}$ and $R^{11}$ may be taken in combination to form a ring.

In the general formula (IV), $R^9$ and $R^{12}$ are preferably an aromatic group having a hydrocarbon group and particularly a 2,6-diisopropylphenyl group. The aliphatic hydrocarbon group having from 1 to 20 carbon atoms may be a linear or branched alkyl group having from 1 to 20 carbon atoms or a cycloalkyl group having from 3 to 20 carbon atoms, specifically a methyl group, an ethyl group, an n-propyl group, an isopropyl group, an n-butyl group, an isobutyl group, a sec-butyl group, a tert-butyl group, a pentyl group, a hexyl group, an octyl group, a decyl group, a dodecyl group, a tetradecyl group, a hexadecyl group, an octadecyl group, a cyclopentyl group, a cyclohexyl group and a cyclooctyl group. A suitable substituent such as a lower alkyl group may be incorporated into the ring of the cycloalkyl group.

As the aromatic group having from 7 to 20 carbon atoms in total and having a hydrocarbon group on the nucleus thereof, there may be mentioned, for example, an aromatic group, such as a phenyl group or a naphthyl group, and an aromatic group having an aromatic nucleus, such as phenyl or naphthyl, into which at least one linear, branched or cyclic alkyl group with 1 to 10 carbon atoms is introduced.

The hydrocarbon group having from 1 to 20 carbon atoms for $R^{10}$ and $R^{11}$ may be a linear or branched alkyl group having from 1 to 20 carbon atoms, a cycloalkyl group having from 3 to 20 carbon atoms, an aryl group having from 6 to 20 carbon atoms or an aralkyl group having from 7 to 20 carbon atoms. The linear or branched alkyl group having from 1 to 20 carbon atoms and the cycloalkyl group having from 3 to 20 carbon atoms may be those exemplified above in connection with the aliphatic hydrocarbon group having from 1 to 20 carbon atoms for $R^9$ and $R^{12}$. The aryl group having from 6 to 20 carbon atoms may be, for example, a phenyl group, a tolyl group, a xylyl group, a naphthyl group or a methylnaphthyl group; and the aralkyl group having from 7 to 20 carbon atoms may be, for example, a benzyl group and a phenethyl group.

(c) Carbene-Type Palladium Complex Compound Represented by the Following General Formula (V-a) or General Formula (V-b):

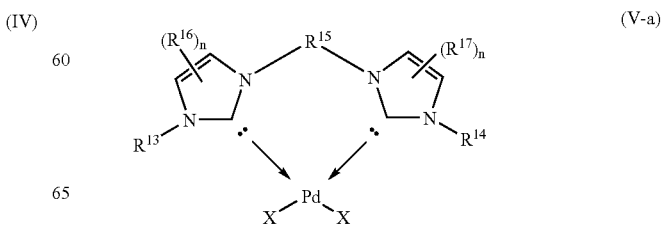

(V-a)

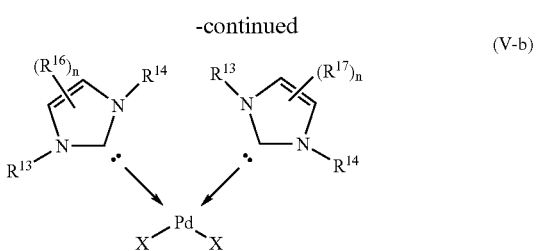

wherein $R^{13}$, $R^{14}$, $R^{16}$ and $R^{17}$ may be the same or different and each represent a hydrogen atom, an alkyl group, an aryl group or an aralkyl group which has from 1 to 20 carbon atoms, which may include —O—, —S— or —NH— and which may contain a halogen substituent; n is an integer of 0 to 2; $R^{15}$ represents an alkylene group or alkylidene group which has from 1 to 20 carbon atoms, which may include —O—, —S— or —NH— and which may contain a halogen substituent; and X is an anion with the proviso that the two X bonded to the same Pd may be the same or different.

The alkyl group, aryl group and aralkyl group having from 1 to 20 carbon atoms for $R^{13}$, $R^{14}$, $R^{16}$ and $R^{17}$ of the formulas (V-a) and (V-b) are not specifically limited and may be, for example, a methyl group, an ethyl group, an n-propyl group, an isopropyl group, an n-butyl group, an isobutyl group, a tert-butyl group, a cyclohexyl group, a phenyl group, a benzyl group, a mesityl group, a tert-octyl group or an α-cumyl group. Above all, a methyl group and a tert-butyl group are preferable. As the alkylene group and alkylidene group having from 1 to 20 carbon atoms for $R^{15}$, there may be mentioned, for example, a methylene group, an ethylene group, a propylene group, a butylene group, an amylene group, a hexylene group, an ethylidene group, a propylidene group, an isopropylidene group, a butylidene group, a benzylidene group and a group having the following structures:

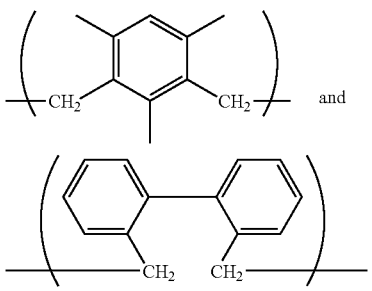

The palladium catalysts described in the foregoing may be used singly or in combination of two or more. The amount of the palladium catalyst may be about 1/1,000,000 mole or more, preferably from about 1/10,000 to about 1/10 mole, per mole of the starting material monohydroxy compound.

If necessary in the present invention, an inorganic redox catalyst and/or an organic redox catalyst as a promoter may be used together with the above palladium catalyst.

Examples of the inorganic redox catalyst include lanthanoid compounds, transition metal compounds of Group V of the Periodic Table, transition metal compounds of Group VI thereof, transition metal compounds of Group VII thereof, iron compounds, cobalt compounds, nickel compounds and copper compounds, which may be in any form of organic complexes, organic salts and inorganic salts. Above all, cerium compounds and manganese compounds are preferable. Specific examples of the cerium compounds include cerium(III) acetate, tris(acetylacetonato)cerium(III), tetra(2,2,6,6-tetramethyl-3,5-heptanedionato)cerium(IV) and tetra (tropolonato)cerium(IV). Suitable examples of the manganese compounds include manganese(II) acetate, tris (acetylacetonato)manganese(III) and tris(2,2,6,6-tetramethyl-3,5-heptanedionato)manganese(IV).

As the organic redox catalyst, there may be mentioned quiones and hydroquinones exhibiting redox catalyst functions. Examples of the organic redox catalyst include 1,4-benzoquinone, 1,2-benzoquinone, 1,4-naphthoquinone, anthraquinone, 1,4-phenanthrenequinone, hydroquinone, catechol, resorcin, 1,4-dihydroxynapthalene, 9,10-dihydroxyanthracene and 1,4-dihydroxyphenanthrene.

The above redox catalysts may be used singly or in combination of two or more. The amount of the redox catalyst may be about 0.1 to 100 moles, preferably about 0.5 to 50 moles, per mole of the main palladium catalyst.

In the process for producing a carbonic ester according to the present invention, an onium salt may be used, if necessary, as an organic salt having a function to activate the starting material monohydroxy compound. As the onium salt, there may be mentioned an ammonium salt, an oxonium salt, a sulfonium salt, a phosphonium salt or a selenonium salt. Above all, an ammonium salt and a phosphonium salt are preferable and a phosphonium salt is more preferable.

As the ammonium salt, there may be used, for example, tetra(n-butyl)ammonium bromide, bis(triphenylphosphoranilidene)ammonium bromide or tetra(n-butyl)ammonium iodide. As the phosphonium salt, there may be used, for example, tetra(n-butyl)phosphonium bromide, tetra(n-butyl) phosphonium iodide, tetraphenylphosphonium bromide or tetraphenylphosphonium iodide.

The amount of the onium salt may be about 0.1 mole % or more based on the hydroxy compound.

As a promoter, heteropolyacid or an onium salt of heteropolyacid may be further suitably used.

As the heteropolyacid, there may be used tungstophosphoric acid, molybdophosphoric acid, tungstosilicic acid, molybdosilicic acid, molybdotungstophosphoric acid, molybdotungstosilicic acid or vanadomolybdophosphoric acid. Further, onium salts, alkali metal salts, alkaline earth metal salts and transition metal salts of these heteropolyacids may also be used. These compounds may be used singly or in combination of two or more.

In the process for producing a carbonic ester according to the present invention, water is by-produced during the reaction. When the amount of the by-product is so much that it adversely affect the reaction, it is preferable to continuously remove the by-product water from the reaction system. Various customarily known methods for removing by-product water from a reaction system may be used, though the addition of a dehydrating agent together with the above palladium catalyst and other promoters is preferable. Examples of the particularly preferred dehydrating agent include inorganic dehydrating agents such as molecular sieves (zeolite), calcium chloride, calcium oxide, diphosphorus pentoxide, sodium hydride and anhydrous sodium hydroxide, and organic dehydrating agents such as acetaldehyde dimethylacetal, acetaldehyde diphenylacetal, acetone dimethylacetal and acetone diphenylacetal. These dehydrating agents may be used in the form of either chips or powders.

Zeolite used as the dehydrating agent has a particle diameter of 300 μm or smaller, preferably 200 μm or smaller, more preferably 100 μm or smaller. Examples of natural zeolite include analcime, faujasite, natrolite, mordenite, clinoptilolite and erionite. Examples of synthetic zeolite include A-type, N-A-type, X-type, Y-type, ZK-type, S-type, T-type, L-type, ZSM-type, AZ-type, NU-type, P-A-type, P-C-type, P-G-type and zeolon. Above all, molecular sieves of synthetic zeolite are preferable, particularly A-3 and A-4 are preferable, and A-3 is more preferable.

The process for producing a carbonic ester according to the present invention comprises reacting an aromatic monohydroxy compound or an aliphatic monohydroxy compound with carbon monoxide and oxygen in the presence of a palladium catalyst and, if necessary, a promoter and a dehydrating agent using a specific reaction solvent which is a compound having a carbonate bond.

The reaction temperature in the process of the present invention is 30 to 180° C., preferably 50 to 150° C., more preferably 80 to 120° C. When the temperature is less than 30° C., there is a possibility that the reaction does not proceed. A temperature beyond 180° C. is not preferable because there is a possibility that side reactions and coloring of the product occur. The reaction pressure is generally under pressurized conditions, since gaseous raw materials such as carbon monoxide and oxygen are used. The carbon monoxide partial pressure is within the range of $1 \times 10^{-2}$ to 20 MPa, preferably within the range of $1 \times 10^{-2}$ to 10 MPa, while the oxygen partial pressure is within the range of $1 \times 10^{-2}$ to 10 MPa, preferably within the range of $1 \times 10^{-2}$ to 5 MPa. In particular, the oxygen partial pressure is desired to be adjusted so that the composition of the gases among the reaction system does not fall within the range in which explosion will occur. When the above reaction pressure is excessively low, the reaction rate will be reduced. On the other hand, too high a pressure is economically disadvantageous because a large apparatus is required to cause expensive equipment costs. When an inert gas or hydrogen is used, the partial pressure thereof is not specifically limited and may be a suitable practical range. The reaction time is, for example, 1 to 48 hours, preferably 2 to 36 hours, more preferably 3 to 24 hours, in the case of a batch system. A reaction time of less than 1 hour will result in a low yield, while a reaction time in excess of 48 hours will not give any additional increase in the yield.

As to the reaction mode, any of a batch system, a semi-continuous system in which the raw materials, catalyst, etc. are continuously fed to a reactor, and a continuous system in which the raw materials, catalyst, etc. are continuously fed to a reactor while continuously drawing out the reaction product therefrom, may be adopted. The condition of the catalyst composition in the reaction system may be either homogeneous or heterogeneous and may be chosen by suitably selecting the catalyst composition. When the catalyst composition is used in a heterogeneous state, the catalyst composition may be suspended in a reaction system. In this case, the catalyst is separated after the reaction by any suitable operation such as filtration. Alternatively, the catalyst composition may be filled in or bound to a reactor or reaction vessel, through which a reaction liquid is passed.

The process for producing a carbonic ester according to the present invention uses an aromatic monohydroxy compound or an aliphatic monohydroxy compound, carbon monoxide and oxygen as raw materials and comprises reacting the raw materials in the presence of the above catalyst composition using a specific solvent which is a compound having a carbonate bond, to obtain the carbonic ester. The carbonic ester as the end product may be as follows.

When an aromatic monohydroxy compound is used as a starting material, there may be mentioned an aromatic carbonic ester of the following general formula (VI) as the end product:

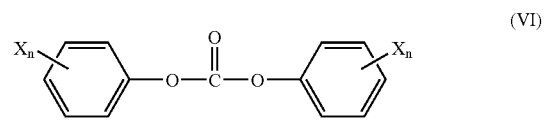

wherein n and X have the same meaning as in the general formula (I).

When an aliphatic monohydroxy compound is used as a starting material, there may be mentioned an aliphatic carbonic ester of the following general formula (VII) as the end product:

wherein R' represents an aliphatic alkyl group having from 1 to 20 carbon atoms, may be primary, secondary and tertiary and may contain a branched structure, a cyclic structure or a halogen atom as appropriate.

As the aromatic dihydroxy compound and aliphatic dihydroxy compound used as a raw material in the process for producing a polycarbonate according to the present invention, there may be used various conventionally known compounds and may be suitably selected according to the desired polycarbonate.

First, the aromatic dihydroxy compound may be an aromatic dihydroxy compound (dihydric phenol) represented by the following general formula (VIII):

wherein Ar represents an arylene group. Specific examples of the aromatic dihydroxy compound include catechol, hydroquinone, resorcin and substituted phenols derived therefrom.

The aromatic dihydroxy compound may be an aromatic dihydroxy compound (dihydric phenol) having from 12 to 27 carbon atoms and represented by the following general formula (IX):

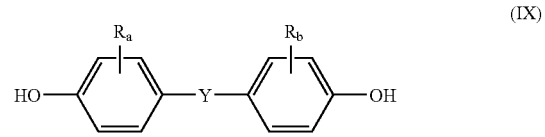

wherein R represents a halogen atom (for example, fluorine, chlorine, bromine or iodine), an alkoxy group, an ester group, a carboxyl group, a hydroxyl group, an alkyl group having from 1 to 8 carbon atoms or an aromatic group having from 6 to 20 carbon atoms in total and containing a hydrogen atom or an alkyl group on its nucleus and may be located at either o-position or m-position, and a and b are each an integer of 0 to 4. When a or b is 2 to 4 in the general formula (IX), plural of R may be the same or different each other. In the general formula (IX), Y represents a direct bond, an alkylene group having from 1 to 8 carbon atoms, an alkylidene group having from 2 to 8 carbon atoms, a cycloalkylene group having from 5 to 15 carbon atoms, a cycloalkylidene group having from 5 to 15 carbon atoms, —S—, —SO—, —SO$_2$—, —O—, —CO— or a group represented by the following general formula:

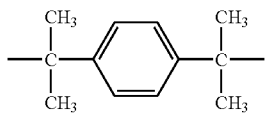

There are various dihydric phenols represented by the above general formula (II). Particularly preferred is 2,2-bis (4-hydroxyphenyl) propane (bisphenol A). As dihydric phenols other than bisphenol A, there may be mentioned bis(4-hydroxyphenyl) compounds (other than bisphenol A) such as 1,1-bis(4-hydroxyphenyl)methane, 1,1-bis(4-hydroxyphenyl)ethane, hydroquinone, 4,4'-dihydroxydiphenyl, bis(4-hydroxyphenyl)cycloalkane, bis(4-hydroxyphenyl)sulfide, bis (4-hydroxyphenyl)sulfone, bis(4-hydroxyphenyl)sulfoxide, bis(4-hydroxyphenyl)ether and bis(4-hydroxyphenyl)ketone; and halogenated bisphenols such as bis(3,5-dibromo-4-hydroxyphenyl)propane and bis(3,5-dichloro-4-hydroxyphenyl)propane. When the above phenols have an alkyl group as a substituent, it is preferred that the alkyl group has from 1 to 6 carbon atoms, particularly from 1 to 4 carbon atoms.

As the aliphatic dihydroxy compound, there may be mentioned an aliphatic dihydroxy compound represented by the general formula:

HOR'OH wherein R' represents an aliphatic alkylene group having from 2 to 20 carbon atoms and may contain a branched structure, a cyclic structure or a halogen atom at any position. Specific examples of the aliphatic dihydroxy compound include ethylene glycol, 1,2-dihydroxypropane, 1,3-dihydroxypropane, 1,2-dihydroxybutane, 1,4-dihydroxybutane, 1,2-dihydroxyhexane, 1,6-dihydroxyhexane, 1,2-dihydroxyoctane, 1,8-dihydroxyoctane, 1,2-dihydroxydecane, 1,10-dihydroxydecane, 1,2-dihydroxydodecane, 1,10-dihydroxydodecane, cyclohexane diol, cyclohexane dimethanol, 1,2-dihydroxy-1-phenylethane, p-(hydroxymethyl)benzyl alcohol.

In the process for producing polycarbonate according to the present invention, it is important that an aromatic dihydroxy compound or an aliphatic dihydroxy compound should be reacted with carbon monoxide and oxygen using a compound having a carbonate bond as a reaction solvent. Although any compound having a carbonate bond may be used as the reaction solvent, the compound must be liquid at the reaction temperature. As the reaction solvent, there may be used the same solvents as described above in connection with the process for producing carbonic esters. Among them, propylene carbonate is preferable. The carbonate solvents may be used singly or in combination of two or more thereof.

In the present invention, the oxidative carbonylation reaction is carried out using the above-described compound having a carbonate bond as the reaction solvent. Therefore, the polymerization reaction can proceed very smoothly so that a polycarbonate having a higher degree of polymerization can be obtained as compared with the case in which an ordinary hydrocarbon solvent or an ether solvent is used. Unlike the conventionally employed halogen-containing organic solvent, there is no fear that the environment is adversely affected by the reaction solvent, since no halogen atom is contained therein.

The palladium catalyst used in the present invention is not specifically limited and a variety of palladium compounds may be used. Thus, ordinary palladium chloride, palladium bromide, palladium carbonyl chloride or palladium acetate may be used.

As other palladium compounds usable as the palladium catalyst in the present invention, there may be further mentioned the following compounds.

(a) Polynuclear Metal Complex Compounds Having a Palladium Atom as a Metal Center and at Least One Atom Exhibiting Lewis Acidity (b) Palladium Complex Compounds Containing as a Ligand an Organic Compound Having at Least Two Nitrogen Atoms As such a palladium complex compound, there may be mentioned palladium complex compounds having a bipyridyl compound as a ligand, palladium complex compounds having a diimine compound as a ligand, and palladium complex compounds having a diamine compound as a ligand.

(c) Carbene-Type Palladium Complex Compounds Represented by the Above General Formula (V-a) or General Formula (V-b)

Details of the compounds (a), (b) and (c) above are the same as those described above in connection with the process for producing carbonic esters.

The palladium catalysts described in the foregoing may be used singly or in combination of two or more. The amount of the palladium catalyst may be about 1/1,000,000 mole or more, preferably from about 1/10,000 to about 1/10 mole, per mole of the starting material dihydroxy compound.

If necessary in the present invention, an inorganic redox catalyst and/or an organic redox catalyst as a promoter may be used together with the above palladium catalyst.

As the inorganic redox catalyst and/or organic redox catalyst, the same compounds as those described above in connection with the process for producing carbonic esters may be used.

The above redox catalysts may be used singly or in combination of two or more. The amount of the redox catalyst may be about 0.1 to 100 moles, preferably about 0.5 to 50 moles, per mole of the main palladium catalyst.

In the process for producing a polycarbonate according to the present invention, an onium salt may be used, if necessary, as an organic salt having a function to activate the starting material dihydroxy compound. As the onium salt, there may be used the same compounds as those described above in connection with the process for producing carbonic esters.

The amount of the onium salt may be about 0.1 mole % or more, preferably about 1 to about 50 mole % based on the hydroxy compound.

Further, other promoters may be used in the present invention for the purpose of improving the catalyst activity, selectivity to the desired product, yield or catalytic life. Any promoter may be used as long as it does not adversely affect the reaction, though a heteropolyacid or an onium salt of a heteropolyacid is suitably used.

As the heteropolyacid, there may be used tungstophosphoric acid, molybdophosphoric acid, tungstosilicic acid, molybdosilicic acid, molybdotungstophosphoric acid, molybdotungstosilicic acid or vanadomolybdophosphoric acid. Further, onium salts, alkali metal salts, alkaline earth metal salts and transition metal salts of these heteropolyacids may also be used. These compounds may be used singly or in combination of two or more.

In the process for producing a polycarbonate according to the present invention, water is by-produced during the reaction. When the amount of the by-product is so much that it adversely affect the reaction, it is preferable to continuously remove the by-product water from the reaction system. Various customarily known methods for removing by-product water from a reaction system may be used, though the addition of a dehydrating agent together with the above palladium catalyst and other promoters is preferable. Examples of the particularly preferred dehydrating agent include inorganic dehydrating agents such as molecular sieves (zeolite), calcium chloride, calcium oxide, diphosphorus pentoxide, sodium hydride and anhydrous sodium hydroxide, and organic dehydrating agents such as acetaldehyde dimethylacetal, acetaldehyde diphenylacetal, acetone dimethylacetal and acetone diphenylacetal. These dehydrating agents may be used in the form of either chips or powders.

In the present invention, an aromatic hydroxy compound (phenol) or an aliphatic hydroxy compound (alcohol) may be added as a terminator.

Examples of the aromatic hydroxy compound include phenols such as phenol, o-, m- and p-cresol, p-tert-butylphenol, p-tert-octylphenol, p-tert-amylphenol, p-α-cumylphenol, methoxyphenol, chlorophenol, trichlorophenol, bromophenol, tribromophenol, fluorophenol and cyanophenol.

Examples of the aliphatic hydroxy compound include methanol, ethanol, 1-propanol, 2-propanol, 2-chloro-1-propanol, 1-chloro-2-propanol, 1-butanol, 2-butanol, isobutanol, tert-butanol, 1-pentanol, 2-methyl-1-butanol, 3-methyl-1-butanol, 2,2-dimethyl-1-propanol, cyclopentanol, 1-hexanol, 2-methyl-1-pentanol, 3-methyl-1-pentanol, 4-methyl-1-pentanol, 2,2-dimethyl-1-butanol, 2,3-dimethyl-1-butanol, 3,3-dimethyl-1-butanol, 2-ethyl-1-butanol, 3-ethyl-1-butanol, cyclohexanol, 1-octanol, 2-octanol, 2-ethyl-1-hexanol, 1-decanol, 2-decanol, 1-dodecanol, 2-dodecanol, 1-tetradecanol, 2-tetradecanol, 1-hexadecanol, 2-hexadecanol, 1-octadecanol, 2-octadecanol and benzyl alcohol.

The process for producing a polycarbonate according to the present invention comprises reacting an aromatic dihydroxy compound or an aliphatic dihydroxy compound with carbon monoxide and oxygen in the presence of a palladium catalyst and, if necessary, a promoter and a dehydrating agent using a specific reaction solvent which is a compound having a carbonate bond.

The reaction temperature in the process of the present invention is 30 to 180° C., preferably 50 to 150° C., more preferably 80 to 120° C. When the temperature is less than 30° C., there is a possibility that the reaction does not proceed. A temperature beyond 180° C. is not preferable because there is a possibility that side reactions and coloring of the product occur. The reaction pressure is generally under pressurized conditions, since gaseous raw materials such as carbon monoxide and oxygen are used. The carbon monoxide partial pressure is within the range of $1\times10^{-2}$ to 20 MPa, preferably within the range of $1\times10^{-2}$ to 10 MPa, while the oxygen partial pressure is within the range of $1\times10^{-2}$ to 10 MPa, preferably within the range of $1\times10^{-2}$ to 5 MPa. In particular, the oxygen partial pressure is desired to be adjusted so that the composition of the gases among the reaction system does not fall within the range in which explosion will occur. When the above reaction pressure is excessively low, the reaction rate will be reduced. On the other hand, too high a pressure is economically disadvantageous because a large apparatus is required to cause expensive equipment costs. When an inert gas or hydrogen is used, the partial pressure thereof is not specifically limited and may be a suitable practical range. The reaction time is, for example, 1 to 48 hours, preferably 2 to 36 hours, more preferably 3 to 24 hours, in the case of a batch system. A reaction time of less than 1 hour will result in a low yield, while a reaction time in excess of 48 hours will not give any additional increase in the yield.

As to the reaction mode, any of a batch system, a semi-continuous system in which the raw materials, catalyst, etc. are continuously fed to a reactor, and a continuous system in which the raw materials, catalyst, etc. are continuously fed to a reactor while continuously drawing out the reaction product therefrom, may be adopted. The condition of the catalyst composition in the reaction system may be either homogeneous or heterogeneous and may be chosen by suitably selecting the catalyst composition. When the catalyst composition is used in a heterogeneous state, the catalyst composition may be suspended in a reaction system. In this case, the catalyst is separated after the reaction by any suitable operation such as filtration. Alternatively, the catalyst composition may be filled in or bound to a reactor or reaction vessel, through which a reaction liquid is passed.

The process for producing a polycarbonate according to the present invention uses an aromatic dihydroxy compound or an aliphatic dihydroxy compound, carbon monoxide and oxygen as raw materials and comprises reacting the raw materials in the presence of the above catalyst composition using a specific solvent which is a compound having a carbonate bond, to obtain the polycarbonate. The polycarbonate as the end product may be as follows.

When an aromatic dihydroxy compound is used as a starting material, there may be mentioned an aromatic polycarbonate of the following general formula (X) as the end product:

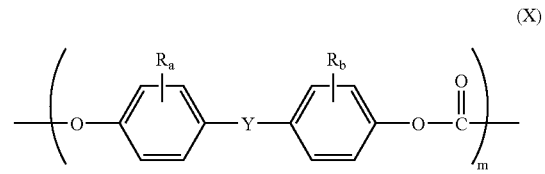

wherein R, a, b and Y have the same meaning as in the general formula (IX) and m is an integer of 1 or more and varies depending upon the molecular weight of the product. The structure of the termini of the molecule is not specifically limited.

When an aliphatic dihydroxy compound is used as a starting material, there may be mentioned an aliphatic polycarbonate of the following general formula (.) as the end product:

wherein R' represents an aliphatic alkylene group having from 2 to 20 carbon atoms and may contain a branched structure, a cyclic structure, an aromatic ring or a halogen atom, and n is an integer of 1 or more and varies depending upon the molecular weight of the product. The structure of the termini of the molecule is not specifically limited.

EXAMPLES

The present invention will be described in further detail below by way of Examples and Comparative Examples. However, the present invention is not restricted by these Examples in any way.

The catalytic components and reagents used in the following examples are commercially available products or prepared in accordance with the methods disclosed in literatures.

Illustrated by Reference Examples are cases in which dichloromethane that is considered to give a high yield but to adversely affect the environment is used and cases in which the particle diameter of zeolite does not fall within the scope of claim 7 (claiming the particle diameter as 300 µm or smaller).

The yield of carbonic ester (diphenyl carbonate) was measured by gas chromatography using an internal standard method on the basis of the starting material (phenol).

Example 1

In a stainless steel autoclave as a reactor with a capacity of containing 30 milliliter, 8.32 millimole of phenol, palladium (II) acetate (5.6 mg, 0.025 millimole), cerium(III) acetate monohydrate (42 mg, 0.125 millimole), tetrabutylammonium bromide (202 mg, 0.625 millimole), benzoquinone (68 mg, 0.625 millimole), molecular sieve 3A1/16 (Lot: WTQ3229, available from Wako Pure Chemical Industries, Ltd., 1.0 g) and propylene carbonate (10 ml) were charged. A nitrogen gas was fed into the autoclave to replace the gas existing in the reactor. Thereafter, the autoclave was pressurized with carbon monoxide and evacuated so that the nitrogen was replaced with carbon monoxide. Then, the autoclave was pressurized with carbon monoxide to 6.0 MPa at 25° C. Further, oxygen was fed to the autoclave so that the total pressure became 6.3 MPa. The resulting reactor was placed in an oil bath provided with a magnetic stirrer and the reaction was performed with heating at the temperature of 100° C. for 3 hours with stirring. After completion of the reaction, the molecular sieve was removed and the solvent was removed by distillation to obtain a crude product. The yield of diphenyl carbonate was 45%.

Comparative Example 1

Comparative Example 1 was conducted in a similar manner as Example 1 except that the propylene carbonate as a reaction solvent was replaced by acetophenone in which phenol as a starting material and diphenyl carbonate as a product were able to be dissolved. The yield of diphenyl carbonate was 3%.

Reference Example 1

Reference Example 1 was conducted in a similar manner as Example 1 except that the propylene carbonate as a reaction solvent was replaced by dichloromethane being a halogen-containing solvent. The yield of diphenyl carbonate was 44%.

Example 2

Example 2 was conducted in a similar manner as Example 1 except that palladium(II) acetate was replaced by (6,6'-dimethyl-2,2'-bipyridyl)palladium chloride complex. The yield of diphenyl carbonate was 49%.

Comparative Example 2

Comparative Example 2 was conducted in a similar manner as Example 2 except that the propylene carbonate as a reaction solvent was replaced by acetophenone. The yield of diphenyl carbonate was 4%.

Example 3

Example 3 was conducted in a similar manner as Example 1 except that palladium(II) acetate was replaced by 2,2'-biquinoline palladium chloride complex. The yield of diphenyl carbonate was 47%.

Comparative Example 3

Comparative Example 3 was conducted in a similar manner as Example 3 except that the propylene carbonate as a reaction solvent was replaced by acetophenone. The yield of diphenyl carbonate was 3%.

Example 4

Example 4 was conducted in a similar manner as Example 1 except that palladium(II) acetate was replaced by 2,9'-dimethyl-1,10-phenanthrolin palladium chloride complex. The yield of diphenyl carbonate was 50%.

Comparative Example 4

Comparative Example 4 was conducted in a similar manner as Example 4 except that the propylene carbonate as a reaction solvent was replaced by acetophenone. The yield of diphenyl carbonate was 5%.

Example 5

Example 5 was conducted in a similar manner as Example 1 except that tetrabutylammonium bromide was replaced by tetrabutylphosphonium bromide. The yield of diphenyl carbonate was 48%.

Comparative Example 5

Comparative Example 5 was conducted in a similar manner as described except that the propylene carbonate as a reaction solvent was replaced by acetophenone. The yield of diphenyl carbonate was 3%.

Example 6

Example 5 was conducted in a similar manner as Example 5 except that the molecular sieve 3A1/16 was replaced by synthetic zeolite A-3 powder (Lot: LDJ2509, available from Wako Pure Chemical Industries, Ltd., particle diameter: below 75 µm). The yield of diphenyl carbonate was 70%.

Reference Example 2

Reference Example 2 was conducted in a similar manner as Example 5 except that the molecular sieve 3A1/16 was replaced by synthetic zeolite A-3 particle-type (Lot: LDJ2509, available from Wako Pure Chemical Industries, Ltd., particle diameter: 500 µm to 1.18 mm). The yield of diphenyl carbonate was 18%.

Example 7

Example 7 was conducted in a similar manner as Example 5 except that the molecular sieve 3A1/16 was replaced by synthetic zeolite A-3 powder (Lot: LDJ2509, available from Wako Pure Chemical Industries, Ltd., particle diameter: below 75 µm). The yield of diphenyl carbonate was 80%.

Reference Example 3

Reference Example 3 was conducted in a similar manner as Example 5 except that the molecular sieve 3A1/16 was replaced by synthetic zeolite A-3 particle-type (Lot:

LDJ2509, available from Wako Pure Chemical Industries, Ltd., particle diameter: 500 μm to 1.18 mm). The yield of diphenyl carbonate was 18%.

Example 8

Example 8 was conducted in a similar manner as Example 5 except that the molecular sieve 3A1/16 was replaced by synthetic zeolite A-3 powder (Lot: SEF2688, available from Wako Pure Chemical Industries, Ltd., particle diameter: below 75 μm). The yield of diphenyl carbonate was 55%.

Reference Example 4

Reference Example 4 was conducted in a similar manner as Example 1 except that the molecular sieve 3A1/16 was replaced by synthetic zeolite A-4 particle-type (Lot: CKP3827, available from Wako Pure Chemical Industries, Ltd., particle diameter: 500 μm to 1.18 mm). The yield of diphenyl carbonate was 10%.

Example 9

In a stainless steel autoclave as a reactor with a capacity of containing 30 milliliter, and having a magnetic stirrer bar, bisphenol A (0.950 g, 4.16 millimole), palladium(II) acetate (5.6 mg, 0.025 millimole), cerium(III) acetate monohydrate (42 mg, 0.125 millimole), tetrabutylammonium bromide (202 mg, 0.625 millimole), benzoquinone (68 mg, 0.625 millimole), molecular sieve 3A (1.0 g) and propylene carbonate (10 ml) were charged. A nitrogen gas was fed into the autoclave to replace the gas existing in the reactor. Thereafter, the autoclave was pressurized with carbon monoxide and evacuated so that the nitrogen was replaced with carbon monoxide. Then, the autoclave was pressurized with carbon monoxide to 6.0 MPa at the temperature of 25° C. Further, oxygen was fed to the autoclave so that the total pressure became 6.3 MPa. The resulting reactor was placed in an oil bath provided with a magnetic stirrer and the reaction was performed with heating at the temperature of 100° C. for 24 hours with stirring. After the reaction, the vessel was cooled and the pressure was released. The contents were taken out by washing with propylene carbonate (30 milliliter) and the molecular sieve was removed by filtration. The filtrate was concentrated in vacuo and poured into an excessively large amount of methanol to obtain precipitates. The precipitates were collected by filtration, washed well with methanol and vacuum-dried for 24 hours to obtain 465 mg of a powdery product (aromatic polycarbonate). From the weight of the polycarbonate obtained, a total mole number of bisphenol A structure contained therein was determined. The yield, calculated on the basis of the mole number of bisphenol A charged, was 44%. The weight average molecular weight (Mw) and number average molecular weight (Mn), when measured by GPC (gel permeation liquid chromatogram, elution liquid: chloroform, column: Shodex K-804L, standard substance: polystyrene), were Mw=3590 and Mn=2630. The aromatic polycarbonate obtained by the foregoing procedures was confirmed, as a result of structural elucidation by IR, NMR, etc., to have the same main chain structure as that of commercially available polycarbonate obtained from bisphenol A. The results of Example 9 are shown in Table 1.

Comparative Example 6

Comparative Example 6 was conducted in a similar manner as Example 9 except that the propylene carbonate as a reaction solvent was replaced by acetophenone in which bisphenol A as a monomer and polycarbonate as a product obtained were able to be dissolved. The results of Comparative Example 6 are shown in Table 1.

Reference Example 5

Reference Example 5 was conducted in a similar manner as Example 9 except that the propylene carbonate as a reaction solvent was replaced by dichloromethane being a halogen-containing solvent. The results of Reference Example 5 are shown in Table 1.

Example 10

Example 10 was conducted in a similar manner as Example 9 except that palladium(II) acetate was replaced by (6,6'-dimethyl-2,2'-bipyridyl)palladium chloride complex. The results of Example 10 are shown in Table 1.

Comparative Example 7

Comparative Example 9 was conducted in a similar manner as Example 10 except that the propylene carbonate as a reaction solvent was replaced by acetophenone. The results of Comparative Example 7 are shown in Table 1.

Example 11

Example 11 was conducted in a similar manner as Example 9 except that palladium(II) acetate was replaced by 2,2'-biquinoline palladium chloride complex. The results of Example 11 are shown in Table 1.

Comparative Example 8

Comparative Example 8 was conducted in a similar manner as Example 11 except that the propylene carbonate as a reaction solvent was replaced by acetophenone. The results of Comparative Example 8 are shown in Table 1.

Example 12

Example 12 was conducted in a similar manner as Example 9 except that palladium(II) acetate was replaced by 2,9-dimethyl-1,10-phenanthrolin palladium chloride complex. The results of Example 12 are shown in Table 1.

Comparative Example 9

Comparative Example 9 was conducted in a similar manner as Example 12 except that the propylene carbonate as a reaction solvent was replaced by acetophenone. The results of Comparative Example 9 are shown in Table 1.

Example 13

Example 13 was conducted in a similar manner as Example 9 except that tetrabutylammonium bromide was replaced by tetrabutylphosphonium bromide. The results of Example 13 are shown in Table 1.

Comparative Example 10

Comparative Example 10 was conducted in a similar manner as Example 13 except that the propylene carbonate as a reaction solvent was replaced by acetophenone. The results of Comparative Example 10 are shown in Table 1.

Example 14

Example 14 was conducted in a similar manner as Example 9 except that the molecular sieve 3A was replaced by synthetic zeolite A-3 powder (Lot: LDJ2509, available from Wako Pure Chemical Industries, Ltd., particle diameter: below 75μ). The results of Example 14 are shown in Table 1.

Example 15

Example 15 was conducted in a similar manner as Example 9 except that palladium(II) acetate was replaced by (6,6'-dimethyl-2,2'-bipyridyl)palladium chloride complex and that the molecular sieve 3A was replaced by synthetic zeolite A-3 powder (Lot: LDJ2509, available from Wako Pure Chemical Industries, Ltd., particle diameter: below 75 μm). The results of Example 15 are shown in Table 1.

Example 16

Example 16 was conducted in a similar manner as Example 9 except that palladium(II) acetate was replaced by 2,2'-biquinoline palladium chloride complex and that the molecular sieve 3A was replaced by synthetic zeolite A-3 powder (Lot: LDJ2509, available from Wako Pure Chemical Industries, Ltd., particle diameter: below 75 μm). The results of Example 16 are shown in Table 1.

Example 17

Example 17 was conducted in a similar manner as Example 9 except that palladium(II) acetate was replaced by 2,9-dimethyl-1,10-phenanthrolin palladium chloride complex and that the molecular sieve 3A was replaced by synthetic zeolite A-3 powder (Lot: LDJ2509, available from Wako Pure Chemical Industries, Ltd., particle diameter: below 75 μm). The results of Example 17 are shown in Table 1.

TABLE 1

| No. | Solvent | Yield (%) | Mn | Mw |
| --- | --- | --- | --- | --- |
| Example 9 | propylene carbonate | 44 | 2630 | 3590 |
| Comparative Ex. 6 | acetophenone | 1 | 440 | 690 |
| Reference Ex. 5 | dichloromethane | 43 | 2220 | 3210 |
| Example 10 | propylene carbonate | 55 | 2760 | 4040 |
| Comparative Ex. 7 | acetophenone | 3 | 550 | 800 |
| Example 11 | propylene carbonate | 55 | 2530 | 4230 |
| Comparative Ex. 8 | acetophenone | 2 | 500 | 770 |
| Example 12 | propylene carbonate | 56 | 2910 | 4990 |
| Comparative Ex. 9 | acetophenone | 2 | 490 | 760 |
| Example 13 | propylene carbonate | 42 | 2590 | 3600 |
| Comparative Ex. 10 | acetophenone | 2 | 500 | 760 |
| Example 14 | propylene carbonate | 71 | 3060 | 4920 |
| Example 15 | propylene carbonate | 86 | 4110 | 7500 |
| Example 16 | propylene carbonate | 77 | 3340 | 5330 |
| Example 17 | propylene carbonate | 88 | 4090 | 8840 |

INDUSTRIAL APPLICABILITY

In accordance with the method of the present invention, without using poisonous phosgene or chlorine gas and without using a halogen-containing organic solvent such as dichloromethane or chloroform which is likely to adversely affect the environment, a carbonic ester can be produced with a higher yield and at a higher reaction rate and, also, a polycarbonate having a higher molecular weight as compared with the conventional method can be produced with a higher yield and at a higher reaction rate.

The polycarbonate thus obtained is a useful resin as a material used in the electric or electronic field, automobile field, optical part field, structural material field, etc.

The invention claimed is:

1. A process for producing a polycarbonate, comprising subjecting an aromatic dihydroxy compound or an aliphatic dihydroxy compound to oxidative carbonylation with carbon monoxide and oxygen in the presence of a palladium catalyst using a compound having a carbonate bond as a reaction solvent,
    wherein the compound having a carbonate bond is selected from the group consisting of propylene carbonate, ethylene carbonate, and mixtures thereof.

2. The process for producing a polycarbonate as defined in claim 1, wherein the aromatic dihydroxy compound or aliphatic dihydroxy compound is subjected to oxidative carbonylation with carbon monoxide and oxygen in the presence of the palladium catalyst and a promoter.

3. The process for producing a polycarbonate as defined in claim 2, wherein the promoter is a redox catalyst.

4. The process for producing a polycarbonate as defined in claim 2, wherein the promoter is an organic salt for activating the aromatic dihydroxy compound or aliphatic dihydroxy compound.

5. The process for producing a polycarbonate as defined in claim 1, wherein the oxidative carbonylation is carried out in a further presence of a dehydrating agent.

6. The process for producing a polycarbonate as defined in claim 1, wherein the compound having a carbonate bond is ethylene carbonate.

7. The process for producing a polycarbonate as defined in claim 1, wherein the compound having a carbonate bond is propylene carbonate.

8. The process for producing a polycarbonate as defined in claim 1, wherein the compound having a carbonate bond is a mixture of propylene carbonate and ethylene carbonate.

9. The process for producing a polycarbonate as defined in claim 1, comprising the aromatic dihydroxy compound.

10. The process for producing a polycarbonate as defined in claim 1, comprising the aliphatic dihydroxy compound.

* * * * *